US008460885B2

(12) United States Patent
Lane et al.

(10) Patent No.: US 8,460,885 B2
(45) Date of Patent: *Jun. 11, 2013

(54) BINDING OF PATHOLOGICAL FORMS OF PRION PROTEINS

(75) Inventors: Amin Reza Lane, Croydon (GB); Christopher J. Stanley, Huntingdon (GB); Stuart Mark Wilson, London (GB)

(73) Assignee: Microsens Biophage Limited, London (GB)

( * ) Notice: Subject to any disclaimer, the term of this patent is extended or adjusted under 35 U.S.C. 154(b) by 204 days.

This patent is subject to a terminal disclaimer.

(21) Appl. No.: 12/644,283

(22) Filed: Dec. 22, 2009

(65) Prior Publication Data

US 2010/0184054 A1     Jul. 22, 2010

Related U.S. Application Data

(63) Continuation of application No. 10/506,131, filed as application No. PCT/GB03/00858 on Feb. 28, 2003, now Pat. No. 7,659,076.

(30) Foreign Application Priority Data

Feb. 28, 2002  (GB) .................................. 0204797.5
Jul. 18, 2002  (GB) .................................. 0216808.6
Dec. 19, 2002  (GB) .................................. 0229614.3

(51) Int. Cl.
*G01N 33/53* (2006.01)
*G01N 33/566* (2006.01)

(52) U.S. Cl.
USPC ............................................ 435/7.1; 436/501

(58) Field of Classification Search
None
See application file for complete search history.

(56) References Cited

U.S. PATENT DOCUMENTS

| 5,216,127 | A | 6/1993 | Hirai et al. |
| 5,846,533 | A | 12/1998 | Prusiner et al. |
| 5,977,324 | A | 11/1999 | Prusiner et al. |
| 6,221,614 | B1 | 4/2001 | Prusiner et al. |
| 6,419,916 | B1 | 7/2002 | Prusiner et al. |
| 6,916,419 | B2 | 7/2005 | Prusiner et al. |
| 7,208,281 | B2 | 4/2007 | Kiesewetter et al. |
| 7,659,076 | B2 | 2/2010 | Lane et al. |
| 2002/0004586 | A1 | 1/2002 | Aguzzi et al. |
| 2005/0084901 | A1* | 4/2005 | Everett et al. ................ 435/7.1 |

FOREIGN PATENT DOCUMENTS

WO     WO 0043782     7/2000

OTHER PUBLICATIONS

Lee et al. Recognition Properties of Antibodies to Pamam Dendrimers and Their Use in Immune Detection of Dendrimers; Biomedical Microdevices, vol. 3, No. 1 (2001) pp. 53-59.*
Supattapone et al. Elimination of Prions by Branched Polyamines and Implications for Therapeutics; Proceedings of the National Academy of Science, vol. 96, No. 25 (1999) pp. 14529-14534.*
Koo et al. Development of a Strepavidin-Conjugated Single-Chain Antibody That Binds *Bacillus cereus* Spores; Applied and Environmental Microbiology, vol. 64, No. 7 (1998) pp. 2497-2502.*
Kornblatt et al. ,"The Fate of the Prion Protein in the Prion/Plasminogen Complex"; Biochemical and Biophysical Research Communications; Apr. 1, 2003; pp. 518-522.
Cuccioloni et al., "Binding of Recombinant $PrP^c$ to Human Plasminogen: Kinetic and Thermodynamic Study Using a Resonant Mirror Biosensor"; Proteins: Structure, Function, and Bioinformatics 58: pp. 728-734; 2005; 2004 Wiley-Liss, Inc.
Brimacombe et al. "Characterization and Polyanion-Binding of Purified Recombinant Prion Protein"; Biochem. J., vol. 342 (1999), pp. 605-613.
Biondi et al. "Abnormal Platelet Aggregation in Patients with Raynaud's Phenomenon"; Journal of clinical Pathology, vol. 42, (1989) pp. 716-718.
Kongtawelert et al. "A Monoclonal antibody that recognizes 2.3-. 2.6- and 4.6- disulphate ester-ring substitution in pyranose-containing polysaccharides". Journal of Immunological Methods. 126 (1990) 39-49.
Serban et al. "Rapid detection of Creutzfeldt-Jakob disease and scrapie prion proteins" Neurology. 40 (Jan. 1990) 110-117.
Fischer et al. "Binding of disease-associated prion protein to plasminogen". Nature. 408 (Nov. 23, 2000) 479-483.
Eight prion strains have $PrP^{sc}$ molecules with different conformations, Jiri Safar, Holger Willie, Vincenza Itri, Darlene Groth, Hana Serban, Marilyn Torchia, Fred E. Cohen & Stanley B. Prusiner, Nature Medicine, vol. 4, No. 10, Oct. 1998 pp. 1157-1165.
Proteinase K-sensitive disease-associated ovine prion protein revealed by conformation dependent immunoassay, Alana M. Thackray, Lee Hopkins and Raymond Bujdoso Biochem J. (2007) 401, 475-483.
Naresh Chennamsetty et al., "Aggregation-Prone Motifs in Human Immunoglobulin G," J. Mol. Biol., vol. 391, pp. 404-413 (2009).
Kimon K. Frousios et al., "Amyloidogenic determinants are usually not buried," BMC Structural Biology, vol. 9, No. 44, pp. 1-9 (Jul. 9, 2009).
Satish K. Singh et al., "An Industry Perspective on the Monitoring of Subvisible Particles as a Quality Attribute for Protein Therapeutics," Journal of Pharmaceutical Sciences, vol. 99, No. 8, pp. 3302-3321 (Aug. 2010).
Hanns-Christian Mahler et al., "Protein Aggregation: Pathways, Induction Factors an Analysis," Journal of Pharmaceutical Sciences, vol. 98, No. 9, pp. 2909-2934 (Sep. 2009).
Eva Y. Chi et al., "Physical Stability of Proteins in Aqueous Solution: Mechanism and Driving Forces in Nonnative Protein Aggregation," Pharmaceutical Research, vol. 20, No. 9, pp. 1325-1336 (Sep. 2003).

(Continued)

*Primary Examiner* — Rebecca Prouty
*Assistant Examiner* — Paul Martin
(74) *Attorney, Agent, or Firm* — Pillsbury Winthrop Shaw Pittman LLP

(57) ABSTRACT

A process for the selective binding of an aggregating abnormal form of a protein in the presence of the nonaggregating normal form of the protein, including contacting under selective binding conditions a material containing both the abnormal and normal forms with a binding agent which is a polyionic material having a binding avidity for the aggregating form of the protein as present in the sample.

30 Claims, 1 Drawing Sheet

OTHER PUBLICATIONS

Rajesh Krishnamurthy et al., "The Stability Factor: Importance in Formulation Development," Current Pharmaceutical Biotechnology, vol. 3, pp. 361-371 (2002).

Michael R. Sawaya et al., "Atomic structures of amyloid cross-β spines reveal varied steric zippers," Nature, vol. 447, pp. 453-457 (May 24, 2007).

Arnoldus W. P. Vermeer et al., "The Thermal Stability of Immunoglobulin: Unfolding and Aggregation of a Multi-Domain Protein," Biophysical Journal, vol. 78, pp. 394-404 (Jan. 2000).

U.S. Office Action dated Jan. 9, 2013 in corresponding U.S. Appl. No. 13/183,063.

Byron Caughey et al., "Sulfated Polyanion Inhibition of Scrapie-Associated PrP Accumulation in Cultured Cells," Journal of Virology, vol. 67, No. 2, pp. 643-650 (Feb. 1993).

Stephen Dealler et al., "Pentosan polysulfate as a prophylactic and therapeutic agent against prion disease," IDrugs, vol. 6, No. 5, pp. 470-478 (2003).

U.S. Office Action dated Apr. 15, 2013 in corresponding U.S. Appl. No, 13/183,063.

Jun-ichi Anzai et al., "Layer-by-Layer Construction of Multilayer Thin Films Composed of Avidin and Biotin-Labeled Poly(amine)s," Langmuir, vol. 15, No. 1, pp. 221-226 (1999).

Cristian Ionescu-Zanetti et al., "Monitoring the assembly of Ig light-chain amyloid fibrils by atomic force microscopy," PNAS, vol. 96, No. 23, pp. 13175-13179 (Nov. 9, 1999).

Yuelong Liu et al., "pH-Switchable, Ultrathin Permselective Membranes Prepared from Multilayer Polymer Composites," J. Am. Chem. Soc., vol. 119, No. 37, pp. 8720-8721 (1997).

S.C. Lee et al., "Antibodies to PAMAM Dendrimers: Reagents for Immune Detection, Patterning and Assembly of Dendrimers," Dendrimers and Other Dendritic Polymers, Monsanto Company, St. Louis, Missouri, pp. 559-566 (2001).

* cited by examiner

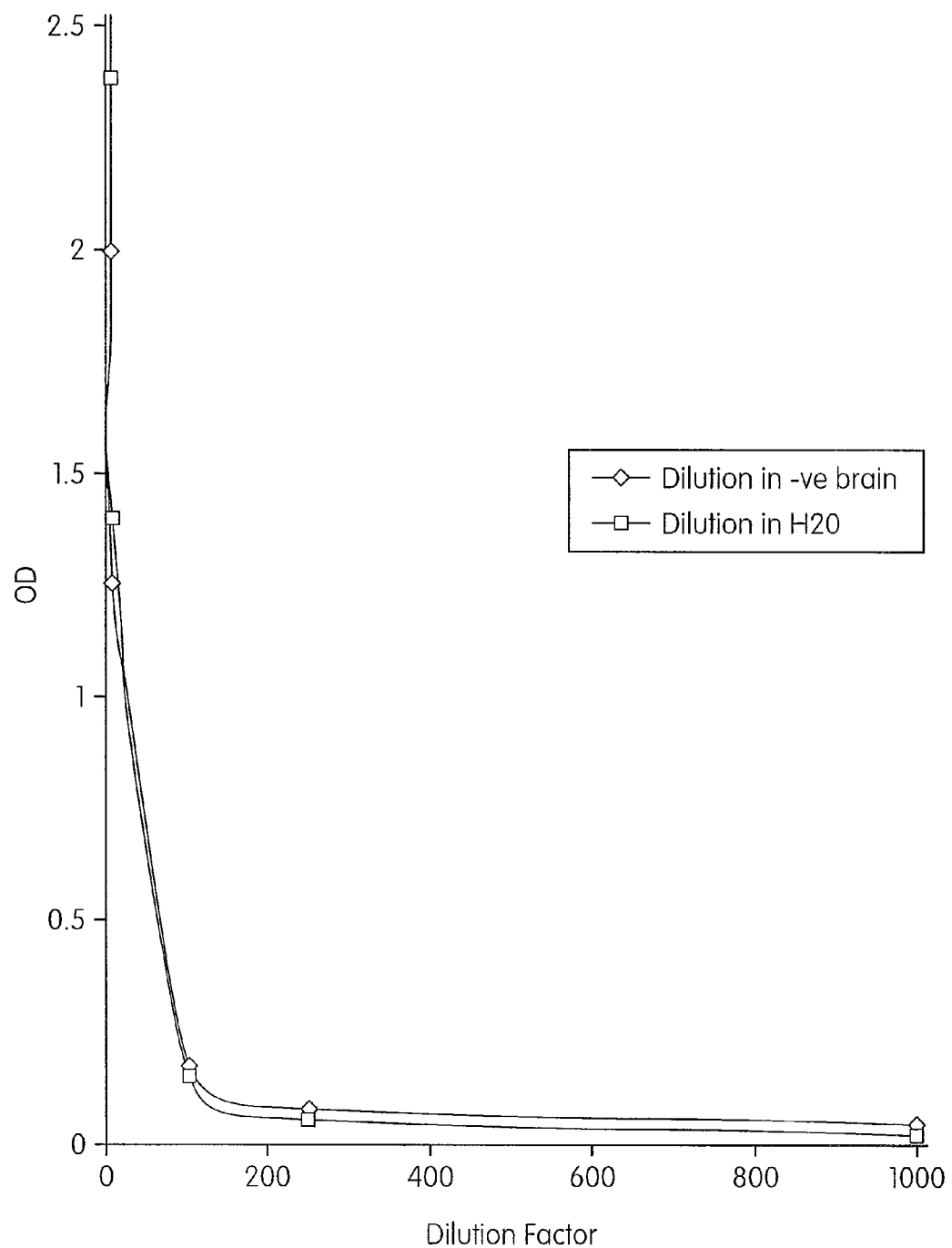

BINDING OF PATHOLOGICAL FORMS OF PRION PROTEINS

This application is a continuation of U.S. application Ser. No. 10/506,131 filed Aug. 27, 2004, which issued as U.S. Pat. No. 7,659,076 on Feb. 9, 2010, which is the National Stage of PCT/GB03/00858, filed Feb. 28, 2003 and for which priority is claimed under 35 U.S.C. §120. This application is based upon and claims the benefit of priority under 35 U.S.C. §119 from the prior Great Britian Patent Application Nos. 0204797.5, filed Feb. 28, 2002, 0216808.6, filed Jul. 18, 2002, and 0229614.3, filed Dec. 19, 2002, the entire contents of all applications are incorporated herein by reference in their entireties.

The present invention relates to the use of protease resistant binding agents, typically polyionic materials such as polyanionic materials including pentosan polysulphate, dextran sulphate or other polyanionic polyglycosides or polycationic materials including polybrene, polyamidoamine dendrimer or poly(diallyldimethylammonium chloride), optionally under selective conditions to capture the pathological or rogue form of the prion protein $PrP^C$ and proteins which are similarly aggregating abnormal forms of proteins which in their normal form are not aggregated.

Prion diseases, also referred to as transmissible spongiform encephalopathies or TSEs, have only been recognised recently. Bovine spongiform encephalopathy (BSE) was first reported in 1985. The first cases of variant Creutzfeldt Jakob disease (vCJD) were reported in 1996. vCJD is a fatal neurodegenerative disease in humans believed to be caused by the consumption of BSE contaminated meat. The incubation time between infection to clinical symptoms in the human may be many years.

The only identified component of the prion, the agent causing prion diseases, is $PrP^{Sc}$, an abnormal isoform of $PrP^C$ ($PrP^{Sc}$ is also referred to as $PrP^{res}$ and $PrP^C$ also referred to as $PrP^{Sen}$). $PrP^{Sc}$ has previously been regarded as being distinguished from $PrP^C$ in that it is comparatively protease resistant. Recently however, it has been published that there is a protease sensitive form of $PrP^{Sc}$, i.e. that there is an infective form of PrP that is protease sensitive.

It may be that the infective but protease sensitive $PrP^{Sc}$ is able to aggregate (i.e. is aggregating in nature) but not yet aggregated or at least only partially aggregated.

Both protease insensitive and protease sensitive forms of $PrP^{Sc}$ and core portions of $PrP^{Sc}$ left after partial protease digestion (often referred to in the art as $PrP^{27-30}$) are referred to herein as $PrP^{Sc}$ except where the context indicates that a specific one of these is meant. Also, the term 'aggregating proteins' is used to include both aggregated protease resistant $PrP^{Sc}$ and similar forms of other proteins as well as infective non-aggregated or partially aggregated forms of $PrP^{Sc}$ or other proteins, which may include the newly observed protease sensitive infective $PrP^{Sc}$.

$PrP^C$ is a GPI anchored glycoprotein of unknown function. Although some other markers for prion diseases have been suggested $PrP^{Sc}$ remains not only an obligatory prion component, but also the only reliable and universally accepted marker for this family of diseases.

The currently favoured methodology for assaying for the presence of $PrP^{Sc}$ is to subject a sample to proteolysis with Proteinase K for a period sufficient to destroy $PrP^C$ and then to determine the presence of surviving $PrP^{Sc}$ by an immunoassay using an antibody which is not selective for $PrP^{Sc}$ in the presence of $PrP^C$ (Serban et al., Neurology, Vol. 40, No. 1, January 1990). The use of the protease naturally excludes the presence of an antibody as a capture agent or as a detection agent during the proteolysis step. The protease must be removed or deactivated before the antibody can be introduced. It would be desirable to avoid this limitation on the procedure.

The assay depends on the complete removal of $PrP^C$ to avoid false positives and upon the conditions not being such as also to degrade $PrP^{Sc}$ to avoid false negatives. Such conditions of selective proteolysis need to be developed for each type of sample to be assayed. The sensitivity of the resulting assay is limited. For instance, in assays of bovine brain tissue, the sensitivity may only be such that a reliable positive result is obtainable at about the time that the animal would have been likely to show clinically observable symptoms of BSE. Thus, the assay has a sensitivity limit in the region of 1 μg/ml, corresponding to $10^4$-$10^5$ prion infectious units.

There is a need for more sensitive and specific diagnostic tests for prion diseases. In particular, an ante-mortem test using blood or other sample types is required to assess the disease status of a particular animal. In the absence of such a method extensive slaughtering of cattle is required once an affected animal is identified within a herd. It is again vital that a diagnostic test is developed to screen the human population and to protect individuals from potential infection from donated blood, surgical procedures and organ and tissue transplants.

U.S. Pat. No. 5,977,324 and U.S. Pat. No. 6,221,614 both describe methods of binding $PrP^{Sc}$ using phosphotungstic acid (PTA). PTA is a non-specific protein precipitant that will also bind to, and precipitate, a wide range of proteins other than $PrP^{Sc}$. The concentration of the proteins in the sample will also greatly affect the recovery using PTA.

Plasminogen has been reported to bind $PrP^{Sc}$ selectively with respect to $PrP^C$ and was proposed for use in diagnostic assays (Fischer et al. Nature, 2000, Nov. 23, 408 (6811): 479-83). However, this method has not proved sufficiently useful in practice. Plasminogen is also identified in a related disclosure, US 2002/0004586, as being a factor which selectively binds $PrP^{Sc}$.

According to U.S. Pat. No. 6,419,916 and related disclosures, the polyamine compound Superfect™ (a branched polyamine mixture produced by heat induced degradation of a PAMAM dendrimer) and other similar branched polyamines are capable of clearing $PrP^{Sc}$ from cells in vitro. The mechanism is unclear. It is speculated that such compounds may bind directly to $PrP^{Sc}$ arranged as an amyloid with exposed negatively charged moieties and induce a conformational change under acidic conditions. It is said that the effect cannot simply involve binding of $PrP^C$ and inhibiting synthesis of $PrP^{Sc}$ because existing $PrP^{Sc}$ is, cleared. The polyamine is found to make $PrP^{Sc}$ protease sensitive provided the pH is below 4. It is deduced that the polyamines act in an acidic cell compartment in the in vitro $PrP^{Sc}$ clearance experiments.

It would appear from this work that it would be speculative to conclude that such polyamines bind $PrP^{Sc}$. A number of other possibilities are advanced. No selectivity for the binding of $PrP^{Sc}$ over $PrP^C$ is shown or suggested. Furthermore, it cannot be deduced that any binding that occurs is more than transitory, just serving to alter the conformation of $PrP^{Sc}$ so as to allow protease attack. Also, the action of the polyamines appears to require a low pH. Our own investigations in fact show that such dendrimer polyamines do not bind $PrP^{Sc}$ at such low pH.

Pentosan polysulphate (poly-b-xylose-2,3-disulphonate, PPS) is one of a range of large polysulphonated polyglycosides (PGs) (MW 8,000-12,000). Made from beechwood, it is an inexpensive compound that has been used for many years as an anticoagulant similar to heparin, also a PG. PGs including PPS and other polyanions are known to bind both $PrP^C$ and recombinant PrP (recPrP), see for instance Brimacombe D B et al, Biochem J, 1999 Sep. 15; 342 pt 3, 605-13. PPS has accordingly been proposed as a potential therapeutic agent for preventing or treating TSE diseases. It has not however been shown to remove existing $PrP^{Sc}$ in vivo or in vitro.

In manufacture, sawdust from beechwood is extracted to produce the soluble sugar polymer of xylose (a five member ring sugar) called pentosan. This polymer is then subjected to a sulphation reaction using a mixture of chlorosulphonic acid and pyridine, which results in 3 out of 4 of all the sugar ring hydroxyls having a sulphate ester added to them. The total sulphate content is then about 50-55% by weight which is more than in heparin, in which it is about 30-35%. The only other similar molecule that approaches this high degree of sulphation is dextran sulphate (40-45%). Pentosan has quite a low MW of 3.5-7.0 K.

No selectivity for binding by polyanions or polycations of $PrP^{Sc}$ with respect to binding of $PrP^C$ has been reported. Surprisingly, we have now established conditions under which polyionic materials bind aggregated altered proteins like $PrP^{Sc}$ and further have established conditions under which such polyanions bind these abnormal forms but do not bind their non-aggregated normal forms like $PrP^C$, the binding being sufficiently strong and under preferred conditions sufficiently selective to be useful in assays for the presence of the aggregated altered protein (e.g. $PrP^{Sc}$).

Accordingly, there is now provided in a first aspect of the invention, a process for the selective binding of an aggregating abnormal form of a protein in the presence of the non-aggregating normal form of the protein, comprising contacting under selective binding conditions a material containing both said abnormal and normal forms with a polyionic material having a binding avidity for said aggregating form of the protein as present in the sample. The binding conditions may include the presence of a competition agent in solution, which competition agent has a lesser binding avidity for the abnormal form of the protein than does the polyionic material.

The polyionic material may be in solution or may provide a surface presenting ionic surface groups. In the latter case, the surface may be that of a polymer having said ionic groups covalently bonded within the structure of the polymer or produced by modification of surface groups of the polymer. An example of a suitable polyanionic polymer is Nafion, a perfluoronated sulphonated hydrocarbon polymer available as beads or as sheets. Polycationic polymers may also be used.

Alternatively, the surface is that of a substrate having coated thereon or bonded thereto a substance presenting said ionic groups. An example of a suitable polymer having such surface groups is a non-charged plastics surface activated with maleic anhydride and derivatised with TRIS to produce surface carboxyl groups or with a polycationic material. Polycations or polyanions may instead be passively coated on polymers such as polystyrene.

In the case of a polyanionic material, whether used in solution or coated on a solid surface, the polyanionic material may preferably be a polyanionic polyglycoside.

Generally, the competition agent has a lesser density of ionic groups than the polyionic material. Without being bound by theory, it is likely that the findings described in detail herein are due to aggregating abnormal forms of protein having more binding sites for interaction with ionic groups than the non-aggregating normal form of the same protein. A competition agent having one or a few ionic groups is able to interact with a certain avidity with either the aggregating or non-aggregating forms of the protein but a polyionic material is able to bind the aggregated form of the protein simultaneously through many ionic groups, leading to it having a higher avidity for the aggregating than for the non-aggregating form.

Our experimental results with infected bovine brains indicate that both immobilised polyanions (such as dextran sulphate) and polycations (such as polyethyleneimine) are able to capture the abnormal form of the prion protein $PrP^{Sc}$ in brain homogenates. The signal obtained using an anti-prion protein antibody/enzyme conjugate is approximately 3 to 5 times higher for the best polycationic capture surface than for the best polyanionic capture surface.

In both cases the detergent Sarkosyl (N-lauroylsarcosine) can act as a competition agent helpful for improving the specificity of capture of the abnormal protein and avoiding a signal from the normal prion protein, when using a non-specific anti-prion protein antibody. Also, partially digesting the sample with trypsin substantially increases the signal from $PrP^{Sc}$ when using either polycationic or polyanionic compounds, but has no effect on specificity (indicating that, under the conditions employed, trypsin is removing an inhibitor of polyion binding of $PrP^{Sc}$, rather than preferentially digesting $PrP^C$, as has been observed for proteinase K).

It is reported in the scientific literature that $PrP^{Sc}$ is natively associated with polyanions such as heparans. It is likely that these negatively charged polymers are interacting with a positively charged region of the $PrP^{Sc}$ structure and there could be multiple interactions with the aggregated proteins.

We propose that a polyanion such as dextran sulphate or pentosan polysulphate is able to bind to the $PrP^{Sc}$ structure with much higher avidity than native heparans and so can displace the endogenous compounds. Thus, highly negatively charged polymers immobilised to a surface can capture specifically the abnormal prion protein. The normal prion protein is non-aggregating and does not have such a high affinity interaction with endogenous heparans or with polyanions such as dextran sulphate. Under the assay conditions chosen the presence of lower affinity anions such as the detergent Sarkosyl improves the specificity of capture still further by competing with the immobilised polyanion for the lower affinity $PrP^C$ interaction sites.

In contrast we suggest that a polycation cannot displace the endogenous heparans from the $PrP^{Sc}$ structure. We suggest that it must instead complex directly with the endogenous heparan/$PrP^{Sc}$ aggregate—forming an ionic interaction with the free negative charges on the heparan. So, in this configuration the native, intact heparan/$PrP^{Sc}$ complex is bound tightly to the immobilised polycation whilst, in the case of an immobilised polyanion the non-native, 'displaced' $PrP^{Sc}$ structure is captured instead. This provides an explanation for the higher signal we obtain with the best polycationic capture surfaces, in that competition by polyanions for endogenous heparans may not be 100% efficient and so not all of the $PrP^{Sc}$ aggregates are bound by negatively charged polymers.

Anionic capture agents may be preferable when the aggregating protein is not expected to be bound natively by native heparan, e.g. when the sample is blood or serum or the like rather than tissue.

In addition to the ionic interactions proposed, there may be additional hydrophobic binding between other regions of the $PrP^{Sc}$ aggregate and the polymers employed. These will strengthen further the binding interactions.

"Avidity" here is used in the usual meaning of the overall binding strength of a molecule with many binding sites with a multivalent binding agent and in contrast to "affinity", being the binding strength between each individual binding site and of the molecule and the binding agent.

The competition agent if used is preferably an amino acid amide of a fatty acid, such as n-lauroylsarcosine. Such materials have detergency properties, but in this context may well simply be acting as monovalent binding agents via their terminal COO⁻ group or as partially polyvalent agents through the formation of micelles.

In a further aspect, the present invention provides a process for the selective binding of an aggregated abnormal form of a protein in the presence of the non-aggregated normal form of the protein, comprising contacting a material containing both said abnormal and normal forms with a polyanionic polyglycoside under conditions such as to provide selective binding of said abnormal form.

In preferred embodiments of each aspect of the invention said abnormal form of a protein is $PrP^{Sc}$ and said normal form is $PrP^{C}$. However, the invention in all its forms is broadly applicable to the selective binding of abnormal aggregating forms of proteins.

Polycationic selective binding agents that can be used include polyethyleneimines, polyamines, including polylysines, polyamidoamines, e.g. PAMAM dendrimers, polyquaternary amines such as poly(diallyldimethylammonium chloride) and 1,5-dimethyl-1,5-diazaundecamethylene polymethobromide (also known as hexadimethrine bromide or Polybrene).

The preferred polyanionic polyglycoside is a polysulphonated polyglycoside. However, other anionic sites such as carboxylic acid groups or phosphate groups may be used as well or instead.

Preferably, the polysulphonated polyglycoside is pentosan polysulphate (PPS) or dextran sulphate.

Other polyanionic pentosan or dextran derivatives may be used as the polyanionic polyglycoside.

A high level of sulphonation (or other anionic group) is preferred.

The levels of sulphonation of the carrageenins, dextrans and pentosan are high. If a low proportion of the potential sulphonation sites is actually taken up by sulphate groups then it may be found that the compounds do not interact with the binding sites in the $PrP^{Sc}$ selectively.

Suitable anionic selective binding agents may include:

Pentosan polysulphate (MW 3500-5000), Dextran sulphate 500 (MW 500,000), Iota-carrageenan, Lambda-carrageenin and carrageenans, e.g. Kappa-carrageenan, Heparins and heparans, Dextran sulphate 8 (MW 8,000), sulphonated polyglycosides such as fucoidan, keratin sulphate, hyaluronic acid polysulphate, colominic acid (bacterial polysialic acid), carrageenan types iii and iv, dermatan sulphate, heparan sulphate, furcellaran, sulphated commerically available polysaccharides e.g. polysorbate, sizofuran, xanthan gum, starch, cellulose compounds, pectin, gastric mucin, ceratonia, agars, acacia gum, Sulphated Glycoside 1, Sulphated Glycoside 2, N-acetyl-D-glucosamines, or Dermatan sulphate L-iduronic acid.

The polyionic material may be one selected to have the ability under non-selective conditions to bind both aggregating altered or rogue forms of a protein and also the non-aggregating normal form of the protein as well as the ability to bind the aggregating form selectively under appropriate conditions.

The desired, selectivity is obtainable by suitable adjustment of the reaction conditions, particularly the presence and concentration of the competition agent, the pH and the detergency. Preferably therefore the pH is so selected as to provide said selective binding.

The pH is preferably from 5.6 to 9, e.g. from 7 to 9, more preferably 8 to 9, e.g. from 8.2 to 8.6, especially 8.4, particularly when the detergents described below are used. Suitable buffers include phosphate buffers and Tris buffers.

The salt concentration is preferably not higher than 250 mM and is preferably significantly less, e.g. not above 100 mM.

Preferably, a detergent is present which promotes said selective binding whether by virtue of detergency or by acting as a competition agent.

Particularly preferred for this purpose are detergents which are an amino acid amide of a fatty acid, e.g. n-lauroylsarcosine or other fatty acid sarcosines. The presence of such a detergent/competition agent is especially, preferred when the selective binding agent is polyanionic.

Preferably the concentration of this detergent is at least 0.05% by weight, more preferably at least 0.1%, preferably at least 0.2%, e.g. 0.2 to 2%, more preferably 0.5 to 1.5%, but greater amounts may be used.

Other detergents having a similar effect may be used, including CHAPS, Brij, Octyl-β-glycoside, Tween 20, Triton X-100 and Nonidet P-40. The use of high concentrations of sodium dodecylsulphate (SDS) is however undesirable. Combinations of n-lauroyl sarcosine (or similar) with other detergents are suitable, preferably containing 0.5 to 2%, e.g. about 1% sarcosine detergent, e.g. with 0.5 to 2%, e.g. about 1%, of one of the detergents listed above, particularly Triton X-100 or Nonidet P-40.

We have found that the presence of trypsin, chymotrypsin, proteinase K, or another such protease can be helpful to prevent inhibition by unknown materials of the binding of aggregating protein to either polyanionic or polycationic selective binding agents. This is especially the case where the sample contains a relatively high level of other proteins, such as is the case if a $PrP^{Sc}$ positive brain sample is diluted with a $PrP^{Sc}$ negative brain material. Additional matrix inhibition prevention can be obtained by including other enzymes of a degradative nature including Dnase and collagenase.

The selective binding agent after binding to said aggregating abnormal form of the protein may be captured with an immobilised capture agent and the presence or amount of a complex formed between said selective binding agent and said capture agent may be determined.

Said capture agent may be a lectin (where the binding agent is suitable, e.g. is a polyglycoside) or an antibody reactive with said selective binding agent. Said selective binding agent may be provided with a selectively bindable tag moiety and said capture agent may then bind to said tag moiety.

Optionally and alternatively, the selective binding agent is immobilised to a solid medium prior to exposure to said sample. The selective binding agent may be provided with a selectively bindable tag moiety and may be immobilised to said solid medium via said tag.

Where a bindable tag moiety is present it may for instance be biotin, fluorescein, dinitrophenol, digoxygenin, or (His)6.

The selective binding agent may be immobilised directly to a solid rather than through a bindable tag. For instance PG's may be directly coupled by covalent coupling through remaining hydroxyl groups of the PG using solid phases derivatised with for instance epoxy or vinyl sulphone groups.

In each aspect of the invention, whether the binding of the abnormal protein takes place before or after the immobilisation or capture of the selective binding agent, the immobilised selective binding agent/abnormal protein complexes are preferably subjected to a washing step to remove normal protein to improve selectivity. The washing step is preferably conducted using a solution containing a said competition agent, which may be a detergent solution, which preferably again comprises a detergent that whether by virtue of its detergency or otherwise promotes selective binding. This is preferably an amino amide of a fatty acid, e.g. n-lauroyl sarcosine or another, fatty acid sarcosine. Preferably, the concentration of the sarcosine detergent in the washing step is at least 0.05%, preferably at least 0.1%, more preferably at least 0.2%, e.g. 0.2 to 2%, preferably 0.5 to 1.5%. Other detergents may also be present and the wash is preferably buffered to a pH in the range of 5.6 to 8.4.

Said binding of $PrP^{Sc}$ (or other abnormal protein) may be qualitatively or quantitatively determined by conducting an immunoassay for $PrP^{Sc}$ (or other aggregating protein) after separation of bound $PrP^{Sc}$ from unbound $PrP^{C}$ (or other normal form protein).

Also, once the aggregating form of the protein has been selectively bound and optionally after the normal form has been removed, further polyanionic material, e.g. anionic polyglycoside (suitably labelled with a tag or detectable label) may be bound to the already bound aggregating protein to form a sandwich (e.g. polyglycoside-aggregated protein-polyglycoside label) which may then be quantitated or detected. Selective binding conditions may not be necessary when carrying out the second part of sandwich formation.

As mentioned above, the selective binding agent may be immobilised to a solid material either before or after being contacted with the altered protein. Separation of the sample from the solid material may then be used to remove the normal form of the protein from the assay leaving only the altered form for further determination.

In this context, solid support materials include not only macroscopic or handlable materials such as microtitre plates, dipsticks and laminar flow devices, but also microbeads and superparamagnetic microbeads, which may be separated off by filtration or by magnetic capture. Biotin or other tags may be conjugated to dextran sulphate or PPS and like materials by standard chemical methods. About one in ten of the sugar backbone residues in PPS is a uronic acid methyl ester and this provides one route for coupling via their carboxyl residues. Other known routes for coupling are hydroxyl (one in four is still free after the sulphation reaction), or end group reducing sugar. Biotin is a convenient bindable tag moiety to employ for binding of the polyanionic material or other selective binding agent to a solid material derivatised with avidin or a material with avidin binding properties such as steptavidin, Neutravidin or Captavidin.

Other molecules suitable for use as bindable tag moieties will include all those which are readily conjugated to the polyionic material and which lend themselves to capture by a suitable capture agent. For instance, a molecule such as fluorescein may be conjugated to PPS or like molecules by reacting an amino fluorescein derivative with the uronic and side chains of pentosan polysulphate in the presence of carbodiimide EDC (1-ethyl-3-(3-dimethyl-aminopropyl)-carbodiimide) and may be captured by a suitable readily available antibody, which may itself be immobilised to the solid material. Other tags suitable for antibody capture in this way include dinitrophenol DNP, digoxygenin, nucleic acid or nucleic acid analog sequences, and (His)6. Binding agents other than antibodies may also be used, e.g. complementary nucleic acid or nucleic acid analog sequences.

Alternatively however, a capture agent may be used which selectively binds the polyionic material itself rather than through a tag moiety. For instance, polyglycosides may be bound by a suitable lectin or by a suitable antibody. Antibodies for binding PPS are for instance disclosed in Kongtawelert et al; J. Immunol. Methods 1990, Jan. 24; 126(1); 39-49. Standard techniques for immobilising such antibodies are well known in the art.

Any known or in future devised method for determining the presence or amount of aggregated or aggregating altered proteins such as $PrP^{Sc}$ (without needing selectivity to exclude the normal form such as $PrP^{c}$) can be used to determine the presence or amount of the aggregating form once it has been selectively bound by the selective binding agent and unbound normal form protein has been separated therefrom, suitably by immobilisation of the bound and washing away of residual unbound. Such methods include the known ELISA, RIA, IRMA and other forms of immunoassay, for instance the method embodied in the Bio-Rad Platelia™ BSE Detection Kit and described in Serban et al.

Depending on the form of the assay used, it may be desired or required to elute the captured abnormal form protein from the selective binding agent prior to the assay. In conducting such an elution step, the presence of a chaotrope such as guanidine thiocynanate may be desirable at a concentration of at least 1M, preferably 2 to 6 M, e.g. 4 to 6 M. Alternative chaotropes may be used including urea.

Additionally or alternatively, a competition agent having a still higher avidity may be used to displace the protein from the selective binding agent. Sodium dodecyl sulphate (SDS) is suitable for this and is preferably used at a concentration of 0.5 to 1% by weight, preferably above 0.75%.

Other proteins that may be selectively bound and determined according to the invention include the β-amyloid protein and tau protein which form plaques in Alzheimer's disease.

Without wishing to be bound by the following theory, it is thought that PPS and similar molecules function in the invention by binding pairs of negative sulphate groups to pairs of positive amino acids (Lys and Arg) in the relevant proteins or via the proteins' polyhistidine metal binding sites. Binding to the aggregated forms may be stronger due to the increased number of binding sites presented by the aggregating protein. Suitable anionic detergents may compete more effectively for binding with the non-aggregating form to enhance selectivity. Suitably, the selectivity obtained is such that the avidity for binding to the aggregating protein is at least three times that for the normal form, preferably at least 10:1.

In a further aspect, the invention includes a process for separating $PrP^{Sc}$ from $PrP^{C}$ comprising selectively binding $PrP^{Sc}$ to a binding agent in the presence of an amino acid amide of a fatty acid. Preferred conditions for such binding are as set out in detail above and the bound protein may be assayed as described.

The invention will be further described and illustrated by the following examples making reference to the accompanying drawing in which:

FIG. 1 shows dilution curves obtained in Example 9.

EXAMPLE 1

Separation of Normal Prion from Rogue Prion Protein Using Biotinylated Pentosan Polysulphate and Subsequent Affinity Capture Introduction Biotin was conjugated to pentosan polysulphate using standard chemical methods. The biotinylated pentosan polysulphate was allowed to bind to the rogue prion protein in brain homogenates and after binding the pentosan polysulphate/prion complexes were captured using streptavidin-derivatised superparamagnetic beads. The captured rogue prion was subsequently eluted from the beads and detected using the immuno-based Bio-Rad Platelia™ BSE Detection Kit; the latter kit is unable to differentiate the normal and rogue prion protein and will give a signal with both proteins. A bank of two BSE-infected and two uninfected bovine brains were investigated and used to demonstrate that the pentosan polysulphate, under the specific conditions described, could be used to specifically capture rogue prion protein from the brain homogenates.

Method

Preparation of the Superparamagnetic Beads

1. Just prior to use, 400 µl of streptavidin superparamagnetic beads (Sigma-Aldrich Company Ltd., S-2415) were washed by magnetic capture in three consecutive 1 ml volumes of TBST (50 mM Tris, 150 mM NaCl, pH 7.5, 0.05% (v/v) Tween20 [Sigma-Aldrich Company Ltd., P-7949]).
2. The beads were finally resuspended in 400 µl of TEST.
3. 100 µl aliquots were prepared in four tubes and the liquid removed. The beads were then ready for use.

Preparation of the Brain Homogenates 1. 300-500 mg of each brain tissue was added to the grinding tubes containing grinding beads as supplied in the BSE Purification Kit (Bio-Rad). The liquid originally supplied in these tubes in the kit was aspirated and discarded prior to use.
2. A volume of 150 mM NaCl that was calculated to generate a 50% (w/v) brain homogenate after homogenisation was added to each tube.
3. The tubes were homogenised for 45 seconds at speed setting 6.5 on a ribolyzer (purchased from Bio-Rad).
4. The homogenates were diluted 1:1 with 150 mM NaCl.
5. 50 µl volumes of each homogenate were placed in separate tubes.

Specific Capture of the Rogue Prion Protein 6. 10 µl of 20% (w/v) N-lauroylsarcosine (Sigma-Aldrich Company Ltd., L-9150) was then added to each tube of homogenate and mixed.
7. 50 µl of biotinylated pentosan polysulphate (10 µg/ml in distilled sterile water) was then added to each tube, mixed and incubated at room temperature for 30 minutes.
8. Each reaction was then added to a tube of washed streptavidin superparamagnetic beads and incubated at room temperature for 30 mins.
9. The beads were then washed by magnetic capture in three 1 ml volumes of TEST.

Elution of the Rogue Prion Protein and Immunodetection

1. Finally, after the last wash, the beads from each reaction were resuspended in 10 µl of C1 (supplied with the Bio-Rad Platelia™ BSE Detection kit).
2. 5 µl of 0.2% (w/v) SDS was added to each bead suspension and mixed.
3. 5 µl of 1M guanidine thiocyanate (Sigma-Aldrich Company Ltd., G-9277) was added to each bead suspension and mixed.
4. The reaction was heated at 100° C. for 5 minutes.
5. 100 µl of R6 (supplied with the Bio-Rad Platelia™ BSE Detection kit) was then added and mixed.
6. 100 µl of each eluate was then used in the Bio-Rad Platelia™ BSE Detection kit using the protocol and reagents supplied with this kit. Briefly, this kit involves immunocapture of normal and/or rogue prion protein and immunodetection with a horseradish peroxidase conjugated antibody.

Results

After performing the immunodetection in the microtiter plate-based Platelia™ assay the signal in each well was measured at a wavelength of 450 nm using an ELISA reader.

| Brain homogenate used | $OD_{450}$ |
|---|---|
| BSE-infected bovine brain sample 1 | 0.229 |
| BSE-infected bovine brain sample 2 | 0.208 |
| Normal bovine brain sample 1 | 0.061 |
| Normal bovine brain sample 2 | 0.047 |

The signal from the two BSE-infected brain homogenates containing rogue prion is significantly higher than in the uninfected normal brain homogenates.

Discussion

The Bio-Rad Platelia™ BSE Detection kit cannot differentiate between normal or rogue prion protein. Normally, the specificity for rogue prion protein is achieved by prior digestion of the sample with proteinase K which removes the protease susceptible normal prion protein. Any rogue prion protein in the sample is more resistant to protease digestion and remains and is subsequently detected by the Platelia™ assay. In this experiment we have demonstrated an alternative approach to protease digestion of the sample. We have used defined conditions under which biotinylated pentosan polysulphate in solution can specifically bind to the rogue prion protein in the sample. The rogue prion/pentosan polysulphate complex can then be captured using streptavidin superparamagnetic beads. After washing, the rogue prion protein can subsequently be eluted and detected in the immunoassay. Normal prion protein is not captured by this protocol and is washed away and is therefore not detected in the immunoassay. We have demonstrated that by using this technique we could correctly detect rogue prion protein in two BSE-infected bovine brains and no signal was observed in two normal bovine brains.

EXAMPLE 2

Separation of Normal Prion from Rogue Prion Protein Using Immobilised Biotinylated Pentosan Polysulphate Introduction Biotin was conjugated to pentosan polysulphate using standard chemical methods. The biotinylated pentosan polysulphate was used to coat streptavidin-derivatised superparamagnetic beads. The coated beads were then used to specifically capture the rogue prion protein from brain homogenates. The captured rogue prion protein was subsequently eluted from the beads and detected using the immuno-based Bio-Rad Platelia™ BSE Detection Kit; the latter kit is unable to differentiate the normal and rogue prion protein and will give a signal with both proteins. A bank of three BSE-infected and three uninfected bovine brains were investigated and used to demonstrate that the pentosan polysulphate, under the specific conditions described, could specifically capture rogue prion protein from the brain homogenates.

Method
Preparation of Pentosan Polysulphate Coated Magnetic Beads
1. 600 µl of streptavidin superparamagnetic beads (Sigma-Aldrich Company Ltd., S-2415) were washed by, magnetic capture in three consecutive 1 ml volumes of TBS (50 mM Tris, 150 mM NaCl, pH 7.5).
2. The beads were finally resuspended in 540 µl of TBS and 60 µl of 10 mg/ml biotinylated pentosan polysulphate in TBS added. The beads were incubated at room temperature for 1 hour with gentle rocking to allow the pentosan polysulphate to coat the beads.
3. After coating the beads were washed by magnetic capture in three consecutive 1 ml volumes of 5% (w/v) bovine albumin (Sigma-Aldrich Company Ltd., A-7906), 50 mM phosphate buffer pH 8.4 and finally resuspended in 60 µl of the same buffer. The beads were then ready for use.

Preparation of the Brain Homogenates
1. 300-500 mg of each brain tissue was added to the grinding tubes containing grinding beads as supplied in the BSE Purification Kit (Bio-Rad). The liquid originally supplied in these tubes in the kit was aspirated and discarded prior to use.
2. A volume of 150 mM NaCl that was calculated to generate a 50% (w/v) brain homogenate after homogenisation was added to each tube.
3. The tubes were homogenised for 45 seconds at speed setting 6.5 on a ribolyzer (purchased from Bio-Rad).
4. The homogenates were diluted 5-fold with 5% (w/v) bovine albumin, 50 mM phosphate buffer pH 8.4.
5. 45 µl volumes of each homogenate were placed in separate tubes.
6. 5 µl of 20% (w/v) SDS (sodium dodecyl sulfate) (Sigma-Aldrich Company Ltd., L-5750) was added to each tube and mixed thoroughly.
7. 450 µl of 5% (w/v) bovine albumin, 50 mM phosphate buffer pH 8.4 was then added to each and mixed.
8. 50 µl of 20% (w/v) N-lauroylsarcosine (Sigma-Aldrich Company Ltd., L-9150) was then added and mixed.

Specific Capture of the Rogue Prion Protein
1. 10 µl of prepared pentosan polysulphate-coated superparamagnetic beads were added to each diluted brain homogenate and incubated with rocking for 1 hour at room temperature.
2. Each reaction was then washed by magnetic capture with 3×100 µl volumes of TBS.

Elution of the Rogue Prion Protein and Immunodetection
1. The beads from each reaction were resuspended in 10 µl of C1 (supplied with the Bio-Rad Platelia™ BSE Detection kit).
2. 5 µl of 0.2% (w/v) SDS was added to each bead suspension and mixed.
3. 5 µl of 1M guanidine thiocyanate (Sigma-Aldrich. Company Ltd., G-9277) was added to each bead suspension and mixed.
4. The reaction was heated at 100° C. for 5 minutes.
5. 100 µl of R6 (supplied with the Bio-Rad Platelia™ BSE Detection kit) was then added and mixed.
6. 100 µl of each eluate was then used in the Bio-Rad.
7. Platelia™ BSE Detection kit using the protocol and reagents supplied with this kit. Briefly, this kit involves immunocapture of normal and/or rogue prion protein and immunodetection with a horseradish peroxidase conjugated antibody.

Results
After performing the immunodetection in the microtiter plate-based Platelia™ assay the signal in each well was measured at a wavelength of 450 nm using an ELISA reader.

| Brain homogenate used | $OD_{450}$ |
|---|---|
| BSE-infected bovine brain sample 1 | 0.465 |
| BSE-infected bovine brain sample 2 | 0.382 |
| BSE-infected bovine brain sample 3 | 0.437 |
| Normal bovine brain sample 1 | 0.060 |
| Normal bovine brain sample 2 | 0.074 |
| Normal bovine brain sample 3 | 0.066 |

The signals from the three BSE-infected brain homogenates containing rogue prion protein is significantly higher than in the uninfected normal brain homogenates.

Discussion
The Bio-Rad Platelia™ BSE Detection kit cannot differentiate between normal or rogue prion protein. Normally, the specificity for rogue prion protein is achieved by prior digestion of the sample with proteinase K which removes the protease susceptible normal prion protein. Any rogue prion protein in the sample is more resistant to protease digestion and remains and is subsequently detected by the Platelia™ assay. In this experiment we have demonstrated an alternative approach to protease digestion of the sample. We have used defined conditions under which pentosan polysulphate can specifically capture the rogue prion protein from the sample. This captured rogue prion protein is eluted and detected in the immunoassay. Normal prion protein is not captured by the pentosan polysulphate and is washed away and is therefore not detected in the immunoassay. We have demonstrated that by using this technique we could correctly detect rogue prion protein in three BSE-infected bovine brains and no signal was observed in three normal bovine brains.

EXAMPLE 3

Biotinylation of PPS

Principle of the Method
Approximately one in ten of the sugar residues in the poly-xylose backbone of pentosan sulphate is substituted with a uronic acid residue, this in turn is substituted with a methyl ester on some of the carboxyl groups, thus a number of free carboxyl groups exist in the molecule and can be derivatised with carbodiimide to form active esters. These in turn may be substituted with amino species to generate an amide bond. In this particular case, EDC and NHS are chosen to form the active ester and biotin hydrazide is chosen as the amino species. Two reactions were performed, a one step reaction in which biotin hydrazide is present initially and no NHS is added, and a second reaction in which NHS/EDC is allowed to react simultaneously with PS and biotin hydrazide.

Materials
Pentosan sulphate (Norton Healthcare) was a gift from Stephen Dealler
Biotin hydrazide 100 mg, Pierce#21339 mw 258.33 batch AH41461
EDC [1-ethyl-3-(3-dimethylaminopropyl)carbodiimide methiodide] Sigma #16, 534-4, 1 g, NHS [N-Hydroxysuccinimide] Sigma #H7377 5 g mw 115.1

Dialysis tubing mwco 3.5 k Pierce #68035

DMSO Sigma

Method

The two reactions were conducted using the following protocols in two versions, with and without NHS:

Dissolve 100 mg of biotin hydrazide in 6 ml of DMSO in a glass vial, this may require warming and/or ultrasonication. The final concentration is thus 16.7 mg/ml or 65 mM. Take 1,000 mg of pentosan sulphate and dissolve in 10 ml of a 50/50 mixture of DMSO and water, this can be done in a plastic universal container. Dissolve 100 mg of EDC in 1 ml of DMSO in a glass vial, it may need warming. Dissolve NHS (approx 40-50 mg) in 1.0 ml of water.

The reaction is performed in conical bottom polystyrene universal containers, with a small circular magnetic stirrer bar (approx 10 mm dia) on a magnetic stirrer base and fitted with a combination pH electrode of 12 mm dia (or less).

EXAMPLE 3a

Reaction without NHS

Place 5.0 ml of pentosan sulphate solution in the reaction vessel, add 1.0 ml of biotin hydrazide solution, stir well and record the pH. A value of 7-8 can be expected. Add 0.2 ml of EDC solution and whilst continuously stirring, record the pH and add 10 uL aliquots of 1 N HCl from a glass micro-syringe and needle, recording the pH after every addition. Continue additions of acid until the pH is in the range 5-6. This is necessary as the reaction generates OH ions. The reaction should remain clear and colourless throughout. If any white precipitate of biotin hydrazide is formed, then the concentration of DMSO should be increased, the target value is >/=50%. Leave the reaction for 2-3 hours at room temperature (or overnight if this is more convenient).

Record the final pH of the reaction mixture. Add an equal volume of 1M NaCl to dilute the DMSO down to 25% and displace conically bound hydrazide and transfer the entire contents to a 35 cm length of 2.2 cm dia dialysis tubing. Note the DMSO concentration is reduced to 25% to avoid damage to the dialysis tubing, the tubing should also be tested with water prior to use to detect any pinholes and should be only ⅓ full to allow for swelling on dialysis. Dialyse overnight against 2 L of water and repeat this several times, the more dialysis the better as pentosan sulphate tends to strongly retain basic ions by non-covalent ionic interaction by virtue of its strong negative charge. Freeze dry the dialysed solution and record the dry weight. The final product should be a firm white cake. Yields can vary a lot, but 50-60% is typical, most of the loss occurs on dialysis, due to MW heterogeneity of the pentosan sulphate and loss of species with a MW of less than 3,500.

EXAMPLE 3b

Reaction with NHS

This reaction is carried out essentially as above except that 1.0 ml (44 mg) of NHS is added to the reaction vial prior to the addition of the EDC reagent which starts the reaction. The initial pH may be in the range of 6-7 and should be adjusted down with 1 N HCl to approx pH 5-6.

Quality Control

After calculating the recovery from the dry weight, make up a solution of 10 mg/ml in water and scan the spectrum from 200 to 400 nm. Peaks should be seen at 260 and 280 nm, though one or both may be unresolved shoulders. This adsorption is due to pyridine residues incorporated into the molecule during the sulphation step. They can be used to monitor the concentration of pentosan sulphate, eg during chromatography. Pentosan can be monitored by UV absorption at 260 nm, or at lower concentrations by the Toluidine Blue metachromasia assay.

EXAMPLE 4

Removal of Prion Protein from Plasma

Removal of the Rogue Prion Protein
1. 100 µl of prepared pentosan polysulphate-coated superparamagnetic beads were added to one of two $PrP^{Sc}$ spiked freshly prepared human plasma aliquots. Both aliquots were incubated with rocking for 1 hour at room temperature.
2. The beads were then removed from the spiked plasma aliquot by magnetic capture. This supernatant, together with the remaining plasma aliquot were then tested for the presence of the rogue prion protein.

Testing of the Spiked Aliquots for Rogue Prion Protein

1. The two plasma aliquots were treated with proteinase K under conditions that we have shown to digest normal prion protein but leave rogue protein intact. These conditions are easily determined empirically. The proteinase K treated samples were then tested for the presence of the rogue prion protein using the immuno-based Bio-Rad Platelia™ BSE Detection kit.

Results

After performing the immunodetection in the microwell plate-based Platelia™ assay the signal in each well was measured at a wavelength of 450 nm using an ELISA reader. The rogue prion protein could be readily detected in the spiked serum sample that had not been treated with pentosan polysulphate. In contrast the pentosan polysulphate-treated sample gave no signal in the test demonstrating that there was no detectable rouge prion protein remaining in this sample.

Discussion

This experiment demonstrates that pentosan polysulphate can be used to effectively remove rogue prion protein from samples of interest.

EXAMPLE 5

Investigation of Detergent Conditions Allowing the Specific Binding of Pentosan Polysulphate to the Rogue Prion Protein Introduction Biotin was conjugated to pentosan polysulphate using standard chemical methods. The biotinylated pentosan polysulphate was used to coat streptavidin-derivatised superparamagnetic beads. The coated beads were then used to establish conditions of detergent under which the pentosan polysulphate could bind the rogue prion protein but not the normal cellular prion protein.

Method

Preparation of Pentosan Polysulphate Coated Magnetic Beads.

1. 600 μl of streptavidin superparamagnetic beads (Sigma-Aldrich Company Ltd., S-2415) were washed by magnetic 0.15 capture in three consecutive 1 ml volumes of TBS (50 mM Tris, 150 mM NaCl, pH 7.5).

2. The beads were finally resuspended in 540 µl of TBS, 5% (w/v) bovine albumin (BSA) (Sigma-Aldrich Company Ltd., A-7906) and 60 µl of 10 mg/ml biotinylated pentosan polysulphate in TBS added. The beads were incubated at room temperature for 1 hour with gentle rocking to allow the pentosan polysulphate to coat the beads.
3. After coating the beads were washed by magnetic capture in three consecutive 1 ml volumes of, 50 mM phosphate buffer pH 8.4, 5% (w/v) BSA and finally resuspended in 60 µl of the same buffer. The beads were then ready for use.

Preparation of the Brain Homogenates
1. 300-500 mg samples of BSE-infected and normal bovine brain tissue were added to the grinding tubes containing grinding beads as supplied in the BSE Purification Kit (Bio-Rad). The liquid originally supplied in these tubes in the kit was aspirated and discarded prior to use.
2. A volume of 150 mM NaCl that was calculated to generate a 50% (w/v) brain homogenate after homogenisation was added to each tube.
3. The tubes were homogenised for 45 seconds at speed setting 6.5 on a ribolyzer (purchased from Bio-Rad).
4. The homogenates were diluted 5-fold with 5% (w/v) BSA, 50 mM phosphate buffer pH 8.4.
5. 45 µl volume aliquots of each homogenate were placed in separate tubes.
6. 5 µl of 20% (w/v) SDS (sodium dodecyl sulfate) (Sigma-Aldrich Company Ltd., L-5750) was added to each tube and mixed thoroughly.
7. 45 µl of 5% (w/v) BSA, 50 mM phosphate buffer pH 8.4 was then added to each aliquot and mixed.
8. 50 µl of N-lauroylsarcosine (Sigma-Aldrich Company Ltd., L-9150) at various concentrations of detergent was then added to various aliquots and mixed. One set (one BSE-infected and one uninfected brain) had no N-lauroylsarcosine added.

Capture of Prion Protein
1. 10 µl of prepared pentosan polysulphate-coated superparamagnetic beads were added to each diluted brain homogenate and incubated with rocking for 1 hour at room temperature.
2. Each reaction was then washed by magnetic capture with 3×100 µl volumes of TBS.

Elution of the Priori Protein and Immunodetection
1. The beads from each reaction were resuspended in 10 µl of C1 (supplied with the Bio-Rad Platelia™ BSE Detection kit).
2. 5 µl of 0.2% (w/v) SDS was added to each bead suspension and mixed.
3. 5 µl of 1M guanidine thiocyanate (Sigma-Aldrich Company Ltd., G-9277) was added to each bead suspension and mixed.
4. The reaction was heated at 100° C. for 5 minutes.
5. 100 µl of R6 (supplied with the Bio-Rad Platelia™ BSE Detection kit) was then added and mixed.
6. 100 µl of each eluate was then used in the Bio-Rad Platelia™ BSE Detection kit using the protocol and reagents supplied with this kit. Briefly, this kit involves immunocapture of normal and/or rogue prion protein and immunodetection with a horseradish peroxidase conjugated antibody.

Results
After performing the immunodetection in the microtiter plate-based Platelia™ assay the signal in each well was measured at a wavelength of 450 nm using an ELISA reader.

| Final concentration of N-lauroylsarcosine in the bead capture buffer | Bovine brain used | $OD_{450}$ |
|---|---|---|
| 2% | BSE-infected brain | 0.52 |
| 2% | Normal brain | 0.14 |
| 1% | BSE-infected brain | 0.33 |
| 1% | Normal brain | 0.13 |
| 0.5% | BSE-infected brain | 0.45 |
| 0.5% | Normal brain | 0.13 |
| 0.2% | BSE-infected brain | 0.41 |
| 0.2% | Normal brain | 0.09 |
| 0% | BSE-infected brain | 0.24 |
| 0% | Normal brain | 0.86 |

At all concentrations of N-lauroylsarcosine there was a discrimination between BSE-infected and normal brain. 0.2% N-lauroylsarcosine was the best concentration of detergent and allowed the pentosan polysulphate to bind to and capture the rogue prion protein without binding or capture of the normal prion protein. In the absence of N-lauroylsarcosine, even though SDS detergent was present, there was no discrimination of pentosan polysulphate binding to rogue prion and normal prion protein. Under these conditions the pentosan polysulphate bound both the normal and rogue prion protein.

Discussion
1. The specificity of binding of pentosan polysulphate to rogue prion protein under these specific test conditions is dependent upon the presence of N-lauroylsarcosine or similar detergents. Without this detergent the pentosan polysulphate bound to both normal and rogue prion protein.

EXAMPLE 6

Investigation of pH Conditions Allowing the Specific Binding of Pentosan Polysulphate to the Rogue Prion Protein Introduction
Biotin was conjugated to pentosan polysulphate using standard chemical methods. The biotinylated pentosan polysulphate was used to coat streptavidin-derivatised superparamagnetic beads. The coated beads were then used to establish conditions of pH under which the pentosan polysulphate could bind the rogue prion protein but not the normal cellular prion protein.

Method
Preparation of Pentosan Polysulphate Coated Magnetic Beads
1. 1 ml aliquots of streptavidin superparamagnetic beads (Sigma-Aldrich Company Ltd., S-2415) were washed by magnetic capture in three consecutive 1 ml volumes of TBS (50 mM Tris, 150 mM NaCl, pH 7.5).
2. Each aliquot of beads were finally resuspended in 1 ml of TBS 5% (w/v) bovine serum albumin (BSA) (Sigma-Aldrich Company Ltd., A-7906) and 100 µl of 10 mg/ml biotinylated pentosan polysulphate in, TBS added. The beads were incubated at room temperature for 1 hour with gentle rocking to allow the pentosan polysulphate to coat the beads.
3. After coating, each aliquot of beads was washed by magnetic capture in three consecutive 1 ml volumes of 5% (w/v) BSA, 50 mM Tris buffer pH 8.4.
4. Aliquots of beads were then resuspended in buffers of pH 5.7, 7.5, 8.4 and 9.6 all containing 5% (w/v) BSA.

Preparation of the Brain Homogenates in Buffers of Various pH
1. 300-500 mg of BSE-infected and normal bovine brain tissue were each added to a grinding tube containing grinding beads as supplied in the BSE Purification Kit (Bio-Rad). The liquid originally supplied in these tubes in the kit was aspirated and discarded prior to use.
2. A volume of 150 mM NaCl that was calculated to generate a 50% (w/v) brain homogenate after homogenisation was added to each tube.
3. The tubes were homogenised for 45 seconds at speed setting 6.5 on a ribolyzer (purchased from Bio-Rad).
4. 50 µl of each homogenate was diluted 5-fold in buffers of pH 5.7, 7.5, 8.4 and 9.6 all containing 5% w/v) BSA.
5. 45 µl volumes of each diluted homogenate were placed in separate tubes.
6. 5 µl of 20% (w/v) SDS (sodium dodecyl sulfate) (Sigma-Aldrich Company Ltd., L-5750) was added to each tube and mixed thoroughly.
7. 45 µl of buffer of the same pH as the initial dilution buffer all containing 5% (w/v) bovine albumin was then added to each and mixed.
8. 50 µl of 20% (w/v) N-lauroylsarcosine (Sigma-Aldrich Company Ltd., L-9150) was then added and mixed.

Bead Capture of the Brain Homogenates
1. 10 µl of prepared pentosan polysulphate-coated superparamagnetic beads in buffer of the corresponding pH were added to each diluted brain homogenate and incubated with rocking for 1 hour at room temperature.
2. Each reaction was then washed by magnetic capture with 3×100 µl volumes of TBS.

Elution of the Rogue Prion Protein and Immunodetection
1. The beads from each reaction were resuspended in 10 µl of C1 (supplied with the Bio-Rad Platelia™ BSE Detection kit).
2. 5 µl of 0.2% (w/v) SDS was added to each bead suspension and mixed.
3. 5 µl of 1M guanidine thiocyanate (Sigma-Aldrich Company Ltd., G-9277) was added to each bead suspension and mixed.
4. The reaction was heated at 100° C. for 5 minutes.
5. 100 µl of R6 (supplied with the Bio-Rad Platelia™ BSE Detection kit) was then added and mixed.
6. 100 µl of each eluate was then used in the Bio-Rad Platelia™ BSE Detection kit using the protocol and reagents supplied with this kit. Briefly, this kit involves immunocapture of normal and/or rogue prion protein and immunodetection with a horseradish peroxidase conjugated antibody.

Results
After performing the immunodetection in the microtiter plate-based Platelia™ assay the signal in each well was measured at a wavelength of 450 nm using an ELISA reader.

| pH buffer used | Bovine brain used | $OD_{450}$ |
|---|---|---|
| 5.7 | BSE-infected brain | 0.79 |
| 5.7 | Normal brain | 0.30 |
| 7.5 | BSE-infected brain | 1.57 |
| 7.5 | Normal brain | 1.25 |
| 8.4 | BSE-infected brain | 0.42 |
| 8.4 | Normal brain | 0.04 |
| 9.6 | BSE-infected brain | 0.08 |
| 9.6 | Normal brain | 0.04 |

At a pH of 7.5 and lower the pentosan polysulphate-coated beads could bind both normal and rogue prion protein. At pHs of 9.6 and higher the pentosan polysulphate-coated beads could not bind both forms of the prion protein. At pH 8.4 the pentosan polysulphate-coated beads captured the rogue prion protein but did not capture the normal prion protein. At this pH the pentosan polysulphate shows specificity for binding to the rogue prion protein.

Discussion
The specificity of binding under the test conditions of pentosan polysulphate to rogue prion protein is dependent upon the pH. At pH 8.4 pentosan polysulphate binds rogue prion protein but cannot bind the normal prion protein. At pHs of 7.5 and lower both normal and rogue prion are bound whereas at pHs of 9.6 and higher there is no binding of rogue or normal prion protein. Therefore, for specific binding of pentosan polysulphate to rogue prion protein under these conditions a pH close to 8.4 should be used.

EXAMPLE 7

Demonstration of Specific Capture of $PrP^{res}$ ($PrP^{Sc}$) to a High Charge Density Polyanionic Ligand Using Competing Lower Charge Density Polyanions to Selectively Inhibit Binding of $PrP^{c}$ Background
PrP can be bound to immobilised polyanions. In the absence of competing polyanions in the capture buffer both $PrP^{res}$ and $PrP^{c}$ are captured. Specificity for capture of $PrP^{res}$ can be achieved by including in the capture buffer a polyanion of lower charge density than that of the capture polyanion. In this example dextran sulphate is used as the high charge density capture polyanion and N-lauroyl sarcosine (which forms multi-molecular detergent micelles) and pentosan polysulphate or fucoidan are used as the weaker charge density competing polyanions.

Method
1. Maxisorp microtitre wells were coated with dextran sulphate (500 000 mwt) following standard procedures.
2. 100 µl of brain homogenate containing 1 mg brain, 50 mM Tris pH 8.3, 1% (w/v) BSA, 1% (v/v) Triton X-100 were added to the coated wells. In some cases this capture buffer also contained either 1% (w/v) N-lauroyl sarcosine, fucoidan, dextran sulphate or various concentrations of pentosan polysulphate.
3. After incubation for 2 hours to allow capture of prion protein, the wells were washed ×3 with 50 mM Tris pH 8.3, 1% (w/v) BSA, 1% (v/v) Triton X-100.
4. The wells were then washed ×3 with PBS.
5. 100 µl of 5M guanidinium thiocyanate was added to each well and incubated 5 mins at 4° C.
6. Wells were washed 3× with PBS and then captured prion protein detected with the anti-prion protein conjugate from the Bio-rad Platelia™ BSE-detection kit following the kit protocol.
7. Developed signal was measured in an ELISA reader at OD450.

Results

| Competing polyanion used | BSE-infected or normal brain | OD450 |
|---|---|---|
| None | BSE-infected | 0.10 |
| None | Normal | 0.15 |

| Competing polyanion used | BSE-infected or normal brain | OD450 |
|---|---|---|
| 1% (w/v) N-lauroyl sarcosine | BSE-infected | 0.95 |
| 1% (w/v) N-lauroyl sarcosine | Normal | 0.03 |
| 1 mg/ml pentosan polysulphate | BSE-infected | 0.26 |
| 1 mg/ml pentosan polysulphate | Normal | 0.03 |
| 0.1 mg/ml pentosan polysulphate | BSE-infected | 0.14 |
| 0.1 mg/ml pentosan polysulphate | Normal | 0.07 |
| 1 mg/ml fucoidan | BSE-infected | 0.13 |
| 1 mg/ml fucoidan | Normal | 0.03 |
| 1 mg/ml dextran sulphate | BSE-infected | 0.02 |
| 1 mg/ml dextran sulphate | Normal | 0.03 |

Discussion

In the absence of competing polyanion in the capture buffer the overall signal is lower and there is no difference in signal from infected or normal brain i.e. there is no specific capture of $PrP^{res}$. The signal from infected brain, however, is increased by including a competing polyanion in the capture buffer and the signal from the corresponding normal or uninfected brain is suppressed. In this example, the best differentiation between infected and normal brain is achieved by the use of 1% (w/v) N-lauroyl sarcosine in the capture buffer. In addition, a differentiation between infected and normal brain can be achieved with fucoidan or pentosan polysulphate. With pentosan polysulphate the differentiation can be increased by increasing the concentration of the competing polyanion, pentosan polysulphate, in the capture buffer from 0.1 to 1 mg/ml. As a control, if dextran sulphate is included in the capture buffer the signal, as expected, is reduced to background as it competes for and inhibits the binding of the PrP to the immobilised dextran sulphate.

EXAMPLE 8

Demonstration of Specific Capture of $PrP^{res}$ to a High Charge Density Polyanion Coated Surface Background In this experiment it was demonstrated that $PrP^{res}$ could be specifically captured to a polyanionic surface. In this instance, the surface was provided by derivatised maleic anhydride polystyrene. Uncharged polysorp and maxisorp wells were used as controls. In other experiments it has been demonstrated that these uncharged surfaces can be derivatised with polyanionic dextran sulphate and can then bind $PrP^{res}$.

Method

1. Maleic anhydride activated polystyrene microplate wells (Perbio Science UK Ltd., Cheshire) were derivatised with TBS 5% (w/v) BSA for 60 mins at room temperature. This generates a carboxyl charged surface on the plastic (see product literature). As non-charged controls, polysorp and maxisorp wells (Nunc) were also investigated. In addition, maxisorp wells were also coated with a polyanionic dextran sulphate ligand using the procedure described in Example 9.
2. 100 μl of brain homogenates containing 1 mg infected or uninfected brain in 50 mM Tris pH 8.3, 1% (w/v) BSA, 1% (v/v) Triton X-100, 1% (w/v) N-lauroyl sarcosine were added to the wells.
3. After incubation for 2 hours to allow capture of prions, the wells were washed ×3 with 50 mM Tris pH 8.3, 1% (w/v) N-lauroyl sarcosine.
4. The wells were then washed ×3 with PBS.
5. 100 μl of 5M guanidinium thiocyanate was added to each well and incubated 5 mins at 4° C.
6. Wells were washed 3× with PBS and then captured prion detected with the anti-prion conjugate from the Bio-Rad Platelia™ BSE-detection kit following the kit protocol.
7. Developed signal was measured in an ELISA reader at OD450.

Results

| Type of wells used | BSE-infected or normal brain | OD450 |
|---|---|---|
| Anionic | BSE-infected | 0.2 |
| Anionic | Normal | 0.03 |
| Polysorp | BSE-infected | 0.05 |
| Polysorp | Normal | 0.03 |
| Maxisorp | BSE-infected | 0.02 |
| Maxisorp | Normal | 0.02 |
| Maxisorp coated with dextran sulphate | BSE-infected | 1.0 |
| Maxisorp coated with dextran sulphate | Normal | 0.02 |

Discussion

The anionic polystyrene surface, under the conditions used in this experiment, specifically captured $PrP^{res}$. Uncharged plastic did not have this effect unless it had been coated with a polyanionic ligand.

EXAMPLE 9

Study of Effects of Dilution of Positive Brain Sample in Negative Sample

Material

Positive Sample: A 25% suspension of brain homogenate known to be positive for $PrP^{sc}$ Negative Sample: A 25% suspension of brain homogenate known to be negative for $PrP^{sc}$ Preparation Maxisorb plates were coated according to the following coating protocol. 1 mg of Polybrene was coated onto the plates in carbonate buffer at pH 7.4 and left overnight, washed 3 times with PBS. The plates were then coated with 1 mg of dextran sulphate in PBS. After 6 hours, the plates were washed 3 times with PBS, then blocked with 5% BSA by adding 400 μl of 5% BSA solution and leaving for 30 minutes. Plates were then washed 3 times with PBS and allowed to dry.

Sample Preparation

Preparation of Sample Dilution in Negative Brain

| sample | Method |
|---|---|
| Neat +ve | 40 μl of +ve sample |
| 1/5 | 8 μl of +ve sample + 32 μl of −ve sample |
| 1/10 | 5 μl of +ve sample + 45 μl of −ve sample |
| 1/100 | 6 μl of (1/10 diluted +ve sample) + 54 μl of −ve sample |
| 1/250 | 20 μl of (1/100 diluted +ve sample) + 30 μl of −ve sample |
| 1/1000 | 10 μl of (1/250 diluted +ve sample) + 30 μl of −ve sample |
| Neat −ve | 25 μl of −ve sample |

Preparation of Sample Dilution in Water

| sample | Method |
|---|---|
| Neat +ve | 40 µl of +ve sample |
| 1/5 | 8 µl of +ve sample + 32 µl of H$_2$O |
| 1/10 | 5 µl of +ve sample + 45 µl of H$_2$O |
| 1/100 | 6 µl of (1/10 diluted +ve sample) + 54 µl of H$_2$O |
| 1/250 | 20 µl of (1/100 diluted +ve sample) + 30 µl of H$_2$O |
| 1/1000 | 10 µl of (1/250 diluted +ve sample) + 30 µl of H$_2$O |

Sample Preparation Prior to Running in Assay

40 µl of sample was mixed with 60 µl of H$_2$O 20 and 25 µl of capture buffer, 250 mM Tris pH 8.4, 5% BSA, 5% Triton X-100, 5% sarkosyl, 1.25 mg/ml trypsin.

Assays were Performed According to the Following Assay Protocol:

1. Add 100 µl of sample to plate and incubate at RT for 120 minutes.
2. Wash×3 with 50 mM Tris pH8.4+1% sarkosyl and ×3 with PBS.
3. Add 100 µl of 4MGuSCN in 20% PEG and incubate for 10 minutes at 2-8° C.
4. Wash×3 with PBS.
5. Add 100 µl of Bio-Rad Platelia™ enzyme antibody conjugate and incubate at 2-8° C. for 60 minutes.
6. Wash×5 with Bio-Rad Platelia™ wash.
7. Add 100 µl of Bio-Rad Platelia™ substrate and incubate for 30 minutes in dark.
8. Add 100 µl of Bio-Rad Platelia™ stop solution and read.

Plate Layout

| | 1 | 1 |
|---|---|---|
| A | Neat +ve | 1/10 In H$_2$O |
| B | 1/5 In negative brain | 1/100 In H$_2$O |
| C | 1/10 in negative brain | 1/250 In H$_2$O |
| D | 1/100 In negative brain | 1/1000 In H$_2$O |
| E | 1/250 in negative brain | |
| F | 1/1000 in negative brain | |
| G | Neat −ve | |
| H | 1/5 In H$_2$O | |

The Results Obtained were as Follows

Dilution of 10 mg of brain homogenate in −ve brain

| sample label | mg of −ve brain | mg of +ve brain | Dilution Factor | OD |
|---|---|---|---|---|
| Neat +ve | 0.00 | 10.00 | 1 | 4 |
| 1/5 | 8.00 | 2.00 | 5 | 1.992 |
| 1/10 | 9.00 | 1.00 | 10 | 1.252 |
| 1/100 | 9.90 | 0.10 | 100 | 0.175 |
| 1/250 | 9.96 | 0.04 | 250 | 0.077 |
| 1/1000 | 9.99 | 0.01 | 1000 | 0.039 |
| Neat −ve | 10.00 | 0.00 | 0 | 0.021 |

Dilution of 10 mg of brain homogenate in H$_2$0

| sample label | mg of −ve brain | mg of +ve brain | Dilution Factor | OD |
|---|---|---|---|---|
| Neat +ve | 0.00 | 10.00 | 1 | 4 |
| 1/5 | 0.00 | 2.00 | 5 | 2.377 |
| 1/10 | 0.00 | 1.00 | 10 | 1.395 |
| 1/100 | 0.00 | 0.10 | 100 | 0.145 |
| 1/250 | 0.00 | 0.04 | 250 | 0.053 |
| 1/1000 | 0.00 | 0.01 | 1000 | 0.016 |

SUMMARY

| | OD | |
|---|---|---|
| mg of +ve brain | Diluted in −ve brain | Diluted in H2O |
| 10.00 | 4 | 4 |
| 2.00 | 1.992 | 2.377 |
| 1.00 | 1.252 | 1.395 |
| 0.10 | 0.175 | 0.145 |
| 0.04 | 0.077 | 0.053 |
| 0.01 | 0.039 | 0.016 |
| 0.00 | 0.021 | — |

These results are presented graphically in FIG. 1, which shows the dilution curves for dilution of positive brain with respectively water and negative brain. The two curves are essentially the same, demonstrating that the presence of negative brain material does not interfere with the assay.

EXAMPLE 10

Capture of Aggregated Tau Protein in Alzheimer's Brain and Normal Age-Matched Controls We have shown that, under defined conditions, various selective capture agents are specific for the capture of aggregated pathogenic prion protein such that normal unaggregated prion is not captured. The aggregated prion protein has an extensive beta-pleated sheet structure whereas normal prion is mostly alpha helix in structure. This example demonstrates that other aggregated beta-pleated sheet proteins such as tau aggregates that are found in Alzheimer's Disease can similarly be selectively captured.

Method 1. 25% (w/v) homogenates of Alzheimer's and age matched control brains were prepared in distilled water.
2. 4 µl of brain was made up to 100 µl in Capture buffer (50 mM Tris pH 8.4, 1% (v/v) Triton X-100, 1% (w/v) N-lauroyl sarcosine, 1% (w/v) BSA).
3. 25 µl of brain was also made up to 100 µl in Capture buffer containing 25 µg Trypsin.
4. Duplicate 100 µl aliquots of brain prepared as in steps 2 and 3 above were added to dextran sulphate-coated microtiter wells and incubated for 2 hours at room temperature.
5. Wells were then washed three times with 50 mM Tris pH 8.4, 1% (w/v) N-lauroyl sarcosine.
6. Samples were incubated with an anti-tau monoclonal antibody in PBS 0.1% (v/v) Tween20.
7. After 1 hour at room temperature wells were washed three times with PBS 0.1% (v/v) Tween20.

8. Immobilised primary antibody was detected with an anti-mouse IgG horseradish peroxidase conjugate following standard procedures.

Results

Results with the Anti-Tau Antibody

| Brain | 1 mg brain No trypsin | 10 mg brain With trypsin |
|---|---|---|
| Alzheimer's 1 | 1.32 | 1.26 |
| Alzheimer's 2 | 0.85 | 0.62 |
| Control 1 | 0.56 | 0.20 |
| Control 2 | 0.97 | 0.51 |

Discussion

It is known that the brains from most aged individuals contain aggregated tau but in Alzheimer's Disease there are more of these aggregates than in age matched controls. Here, the selective capture agent is capturing these aggregates. In this example, trypsin digestion decreases the binding of the protein and reduces the signal but, under these conditions, does not reduce it to back-ground. The ratio of signal after treatment with trypsin to the signal without treatment was much higher in the Alzheimer's brains than in the controls. This suggests that there is more protease resistant aggregates of tau protein in Alzheimer's brain compared to the age matched controls.

EXAMPLE 11

The Effect of Titrating Trypsin on $PrP^{Sc}$ Positive Samples

Method

Dextran Sulphate Coated Plate 1 mg of Hexadimethrine bromide (Polybrene) (100 μl of 10 mg/ml in carbonate buffer pH 7.4) was coated onto Maxisorb plates and left over night at RT°.

Each plate was then washed 3 times with PBS and coated with 1 mg of Dextran Sulphate (MW 500000) (10 mg/ml stock in Tris buffer pH 8.6) and left at RT° for 4 hrs.

The plates were then washed 3 times with PBS and then blocked with 300 μl of 5% BSA solution in TBS and left at RT° for 30 minutes.

The plates were then washed 3 times with PBS.

Capture Buffer 250 mM Tris buffer at pH 8.4, containing 5% BSA, 5% Sarkosyl, 5% Triton Sample Weakly and strongly positive brains BI63 and SV10 (25% homogenate) were treated as follows to provide samples for assay.

25 μl of brain homogenate+25 μl of capture buffer, 250 mM Tris pH 8.4, 5% BSA, 5% Triton X-100, 5% sarkosyl, +65 μl of H$_2$O.

To this sample 10 μl of various concentrations of Trypsin was added.

Wash Buffer 50 mM Tris pH8.4+1% sarkosyl

Method

Assay Protocol

1. Add 100 μl of sample to plate and incubate at RT for 120 minutes.
2. Wash×3 with 50 mM Tris pH8.4+1% sarkosyl and ×3 with PBS.
3. Add 100 μl of 4MGuSCN (in 20% PEG) and incubate for 10 minutes at 2-8° C.
4. Wash×3 with PBS.
5. Add 100 μl of Bio-Rad Platelia™ enzyme antibody conjugate and incubate at 2-8° C. for 60 minutes.
6. Wash×5 with Bio-Rad Platelia™ wash.
7. Add 100 μl of Bio-Rad Platelia™ substrate and incubate for 30 minutes in dark.
8. Add 100 μl of Bio-Rad Platelia™ stop solution and read.

Results 5 mg of Positive brain Bi63

| Trypsin (μg) | OD |
|---|---|
| 1000 | 0.135 |
| 100 | 0.14 |
| 25 | 0.169 |
| 10 | 0.173 |
| 1 | 0.068 |
| 0 | 0.068 |

5 mg of Positive brain SV10

| Trypsin (μg) | OD |
|---|---|
| 25 | 2.858 |
| 0 | 0.894 |

CONCLUSION

The presence of Trypsin appears to have increased the signal. It also appears that a broad concentration range of Trypsin can be used without a detrimental effect on assay.

EXAMPLE 12

Demonstration of the Specific Binding of $PrP^{Sc}$ by Poly Cations

Method

This example demonstrates the use of various poly cations for specific capture of $PrP^{Sc}$. The ligands were either passively coated onto polystyrene microplates or actively coated (i.e. bound), where appropriate, to maleic anhydride plates.

Selective Binding Agent Immobilisation

All the selective binding agents were immobilised overnight at 16-25° C. in 50 mM carbonate buffer pH 9.6 at a concentration of 10 μg/ml. After immobilization, the wells were washed ×3 with PBS and then blocked with 5% (w/v) BSA in PBS for 30 mins. After blocking, wells were washed ×2 with PBS before use. The PAMA dendrimer starbust, poly L-lysine and polyethyleneimine were coated onto both Maxisorp and maleic anhydride microplates whereas the polybreen and pDADMAC were coated onto the Maxisorp plates only.

Capture of $PrP^{Sc}$

1. BSE-infected bovine and uninfected bovine brains were homogenized in distilled water following commercially defined protocols.

2. 0.5 mg of homogenised brain was captured in ligand coated wells in a total volume of 100 µl 50 mM Tris pH 8.3, 1% (w/v) N-lauroyl sarcosine, 1% (v/v) Triton X-100, 1% (w/v) BSA, 0.5 mg/ml trypsin (porcine pancreas).
3. After capture for 2 hours at 18-25° C. the wells were washed ×3 with 50 mM Tris pH 8.3, 1% (w/v) N-lauroyl sarcosine.
4. The wells were then washed ×3 with PBS and incubated for 10 mins with 100 µl of 4M guanidinium thiocyanate, 20% PEG 8000 at 4-8° C.
5. The wells were washed ×3 with PBS and then incubated with an anti-prion monocolonal antibody horseradish peroxidase conjugate.
6. After 60 mins the wells were washed ×5 with PBS 0.1% (v/v) Tween20 and 100 µl TMB substrate added.
7. After 30 mins the OD450 of each reaction was measured and recorded (see table below).

Results

| Binding Agent | Passive adsorption | | Active adsorption | |
|---|---|---|---|---|
| | Positive | Negative | Positive | Negative |
| PAMA dendrimer starburst | 0.938 | 0.030 | 0.097 | 0.026 |
| Polybreen | 0.019 | 0.016 | ND | ND |
| Poly L-lysine | 0.070 | 0.017 | 0.001 | 0.001 |
| pDADMAC* | 1.828 | 0.037 | ND | ND |
| polyethyleneimine | 0.118 | 0.030 | 0.402 | 0.055 |

*Aldrich 40903-0-mw 400,000-500,000

Discussion

The pDADMAC and PAMA dendrimer starburst poly cations work well as $PrP^{Sc}$-specific ligands when passively coated to polystyrene microplates. The pDADMAC works best in this series of binding agents. Polyethyleneimine works to some degree when immobilised on maleic anhydride microplates through its amino groups.

This experiment demonstrates that a variety of poly cations can be used to specifically capture $PrP^{Sc}$ from infected brain under the given Capture Buffer conditions used. These agents can be passively or actively immobilised to polystyrene surfaces. Other experiments have demonstrated that maximum signal from 20 mg of positive brain can be achieved in the presence of 1% (w/v) N-lauroyl sarcosine in the Capture Buffer; without N-lauroyl sarcosine the signal is reduced. This illustrates that the capture agents perform best under defined buffer conditions.

EXAMPLE 13

Capture of Aggregated Beta Amyloid and Tau in Alzheimer's Brain and Normal Age-Matched Controls by Polycationic Binding Agent Background pDADMAC, under defined conditions, has been shown to be specific for the capture of aggregated pathogenic prion protein; normal unaggregated prion is not captured. The aggregated prion protein has an extensive beta-pleated sheet structure whereas normal prion is mostly alpha helix in structure. It is postulated that the binding agent may recognize other aggregated beta-pleated sheet proteins such as beta-amyloid and tau aggregates that are found in Alzheimer's disease. The experiments below were performed in order to investigate this hypothesis.

Method 1. 25% (w/v) homogenates of Alzheimer's and age matched control brains were prepared in distilled water.
2. 80 μl of brain homogenate was made up to 100 μl in Capture buffer (50 mM Tris pH 8.4, 1% (v/v) Triton X-100, 1% (w/v) N-lauroyl sarcosine, 1% (w/v) BSA) and added to polycationic-coated microwells (formed by coating the wells with poly(diallyldimethyl ammonium chloride) (pDADMAC), (Aldrich Chemical Company Inc., catalogue number 40, 903-0).
3. After incubation for 2 hours at room temperature, the wells were washed three times with 50 mM Tris pH 8.4, 1% (w/v) N-lauroyl sarcosine and then incubated with an anti-tau monoclonal antibody in PBS 0.1% (v/v) Tween20.
4. After 1 hour at room temperature wells were washed three times with PBS 0.1% (v/v) Tween20.
5. Immobilised primary antibody was detected with an anti-mouse IgG horseradish peroxidase conjugate following standard procedures.

Results

| Brain | Classification by brain bank | OD450 |
|---|---|---|
| 67/97 | Positive | 1.85 |
| 73/97 | Positive | 0.80 |
| 163/97 | Positive | 0.61 |
| 149/97 | Positive | 0.45 |
| 97/97 | Negative | 0.05 |
| 98/98 | Negative | 0.08 |

Discussion

The polycationic binding agent enables capture of the tau aggregates. When the captured tau is detected with the anti-tau antibody, the Alzheimer's disease brains all gave a high positive signal whereas the negative control brains gave a low negative signal. In conclusion, capture with a polycation under the specified conditions can enable differentiation of Alzheimer's disease brains from those brains without the disease.

EXAMPLE 14

Effect of Different Proteases and DNase on the Matrix Inhibition of pDADMAC Capture of $PrP^{Sc}$ Background The effect of different proteases on the effectiveness of capture of $PrP^{Sc}$ to polycation-coated plates (formed by coating the wells with poly(diallyldimethyl ammonium chloride) (pDADMAC), (Aldrich Chemical Company Inc., catalogue number 40, 903-0) were investigated.

Method 1. 80 μl of brain homogenate was made up to 100 μl by addition of 20 μl of Capture buffer (250 mM Tris pH 8.3, 5% (v/v) Triton X-100, 5% (w/v) N-lauroyl sarcosine, 5% (w/v) BSA) containing different proteases and/or DNase.
2. The homogenates were then added to polycationic-coated microwells.
3. After incubation for 2 hours at room temperature, the wells were washed six times with PBS.

4. 100 μl 4M Guanidine thiocyanate, 20% (w/v) PEG was added to each well.
5. After incubation for 10 minutes at room temperature wells were washed three times with PBS.
6. 100 μl of anti-prion protein horseradish peroxidase conjugate (diluted 1:1500 in PBS 0.1% (v/v) Tween 20 and 5% (w/v) BSA) was added.
7. After 1 hour at room temperature wells were washed five times with PBS 0.1% (v/v) Tween20.
8. Immobilised conjugate was detected with TMB solution following standard protocols.

Results

Assessing Effects of Chymotrypsin, Trypsin, DNase and Proteinase K in Capture Buffer

| Protease or DNase used | Infected bovine brain |
|---|---|
| No protease or DNase | 0.122 |
| Chymo/Trypsin (Conc both 6.25 mg/ml) | 0.139 |
| Dnase/Trypsin (Conc 1 mg/ml Dnase, 6.25 mg/ml Trypsin) | 0.639 |
| Chymo/Dnase (Conc 1 mg/ml Dnase, 6.25 mg/ml Chymo) | 0.616 |
| Chymo/Dnase/Trypsin Conc 1 mg/ml Dnase, 6.25 mg/ml Chymo and Trypsin) | 0.460 |
| Trypsin (Conc 6.25 mg/ml) | 0.568 |
| Chymo (Conc 6.25 mg/ml) | 0.171 |
| Dnase (Conc 1 mg/ml) | 0.180 |
| Proteinase K (Conc 1 mg/ml) | 0.531 |
| Pronase (Conc 1.25 mg/ml) | 0.222 |
| Pronase (Conc 6.25 mg/ml) | 0.178 |

Titrating Trypsin and Chymotrypsin Concentrations in Capture Buffer

| Protease used | Infected bovine brain |
|---|---|
| Trypsin 6.25 mg/ml | 0.732 |
| Trypsin 1.25 mg/ml | 0.726 |
| Chymo 3.125 mg/ml | 0.568 |
| Chymo 0.625 mg/ml | 0.433 |

Discussion

It has been demonstrated that the polycationic ligand under certain conditions is specific for binding to $PrP^{Sc}$. However, the signal can be reduced by matrix effects derived from constituents of the brain homogenate that can interfere with binding and reduce the signal. This matrix effect can be reduced and the signal from infected brain increased by the use of proteases. This study shows that trypsin, chymotrypsin and proteinase K are effective at removing the matrix inhibition; pronase (at the concentrations investigated) is less effective. Trypsin at a concentration of 6.25-1.15 mg/ml is equally effective whereas chymotrypsin is more effective as the concentration is increased. DNase has a demonstrable but smaller effect on removal of matrix inhibition.

EXAMPLE 15

Effect of pH and Salt on pDADMAC Capture of Prion Proteins

Background

The effects of pH and salt concentration on the effectiveness of capture of $PrP^{Sc}$ to polycation-coated plates (formed by coating the wells with poly(diallyldimethyl ammonium chloride) (pDADMAC), (Aldrich Chemical Company Inc., catalogue number 40, 903-0) were investigated Method 1. 80 μl of brain homogenate was made up to 100 μl by addition of 20 μl of Capture buffer (250 mM Tris, see Table for pH, 5% (v/v) Triton X-100, 5% (w/v) N-lauroyl sarcosine, 5% (w/v) BSA and 6.25 mg/ml of Trypsin) containing various concentrations of salt and adjusted to various pHs was investigated.
2. The homogenates were then added to polycationic-coated microwells.
3. After incubation for 2 hours at room temperature, the wells were washed six times with PBS.
4. 100 μl 4M Guanidine thiocyanate, 20% (w/v) PEG was added to each well.
5. After incubation for 10 minutes at room temperature wells were washed three times with PBS.
6. 100 μl of anti-prion protein horseradish peroxidase conjugate (diluted 1:1500 in PBS 0.1% (v/v) Tween 20 and 5% (w/v) BSA) was added.
7. After 1 hour at room temperature wells were washed five times with PBS 0.1% (v/v) Tween20.
8. Immobilised conjugate was detected with TMB solution following standard protocols and the OD450 of the reactions measured.

Results

Effect of pH

| Capture Buffer pH | Infected bovine brain | Negative bovine brain |
|---|---|---|
| 5 | 0.177 | 0.119 |
| 6 | 0.082 | 0.1 |
| 7 | 0.093 | 0.045 |
| 8.4 | 0.226 | 0.039 |
| 9 | 0.24 | 0.038 |
| 10 | 0.25 | 0.037 |

Effect of Salt

| Capture Buffer | Infected bovine brain | Uninfected bovine brain |
|---|---|---|
| 20 mM NaCl | 0.476 | 0.038 |
| 100 mM NaCl | 0.361 | 0.039 |
| 250 mM NaCl | 0.191 | 0.028 |
| 1M NaCl | 0.06 | 0.024 |

Discussion

As the pH of the Capture buffer is lowered the signal from the uninfected brain increases but the signal from the infected brain decreases. At pHs of greater than 8.0 the optimum positive to negative signal ratio is achieved.

As the salt concentration in the Capture buffer is increased the signal from the infected brain progressively decreases. This indicates that a low salt concentration or no salt is the optimum condition for the $PrP^{Sc}$ cap

EXAMPLE 16

Effect of Varying Concentrations of N-lauroyl Sarcosine and Protease on pDADMAC Capture of PrPSc Background The effect of different N-lauroyl sarcosine concentrations in the presence or absence of trypsin were investigated on the effectiveness of capture of PrPSc to polycation-coated plates (formed by coating the wells with poly(diallyldimethyl ammonium chloride) (pDADMAC), (Aldrich Chemical Company Inc., catalogue number 40, 903-0) were investigated.

Method 1. 80 µl of infected brain homogenate was made up to 100 µl by addition of 20 µl of Capture buffer (250 mM Tris pH 8.3, 5% (v/v) Triton X-100, 5% (w/v) BSA) containing different concentrations of protease and N-lauroyl sarcosine.
2. The homogenates were then added to polycationic-coated microwells.
3. After incubation for 2 hours at room temperature, the wells were washed six times with PBS.
4. 100 µl 4M Guanidine thiocyanate, 20% (w/v) PEG was added to each well.
5. After incubation for 10 minutes at room temperature wells were washed three times with PBS.
6. 100 µl of anti-prion protein horseradish peroxidase conjugate (diluted 1:1500 in PBS 0.1% (v/v) Tween 20 and 5% (w/v) BSA) was added.
7. After 1 hour at room temperature wells were washed five times with PBS 0.1% (v/v) Tween20.
8. Immobilised conjugate was detected with TMB solution following standard protocols.

Results

| Detergent and protease used in Capture Buffer | Concentrations of agent used | OD450 |
|---|---|---|
| N-lauroyl sarcosine | 0 | 0.08 |
| Trypsin | 1.25 mg/ml | |
| N-lauroyl sarcosine | 2.5% | 1.181 |
| Trypsin | 1.25 mg/ml | |
| N-lauroyl sarcosine | 5% | 2.267 |
| Trypsin | 1.25 mg/ml | |
| N-lauroyl sarcosine | 10.0% | 2.628 |
| Trypsin | 1.25 mg/ml | |
| N-lauroyl sarcosine | 0 | 0.171 |
| Trypsin | 6.25 mg/ml | |
| N-lauroyl sarcosine | 2.5% | 2.384 |
| Trypsin | 6.25 mg/ml | |
| N-lauroyl sarcosine | 5% | 2.725 |
| Trypsin | 6.25 mg/ml | |
| N-lauroyl sarcosine | 10.0% | 2.883 |
| Trypsin | 6.25 mg/ml | |

Discussion

In the absence of N-lauroyl sarcosine there is no signal from the infected brain with low concentrations of trypsin. At higher concentrations of trypsin, however, some signal is restored in the absence of N-lauroyl sarcosine.

Whilst the invention has been described with particular reference to preferred embodiments thereof it will be appreciated that many modifications and variations thereof are possible within the general scope of the invention. Any variation of the invention as explicitly claimed which would operate in the same way to produce the same result is to be within the protection conferred by the application.

In this specification, unless expressly otherwise indicated, the word ‘or’ is used in the sense of an operator that returns a true value when either or both of the stated conditions is met, as opposed to the operator ‘exclusive or’ which requires that only one of the conditions is met. The word ‘comprising’ is used in the sense of ‘including’ rather than in to mean ‘consisting of’.

The invention claimed is:

1. A process for the selective binding of an aggregating abnormal form of a protein in the presence of the non-aggregating normal form of the protein, comprising contacting under selective binding conditions a material containing both said abnormal and normal forms with a binding agent which is a polyionic material having a binding avidity for said aggregating form of said protein as present in the material, and which is a polyanionic polyglycoside, a polyethyleneimine or a polyamine, or a polymer providing a surface having ionic groups covalently bonded within the structure of the polymer or produced by modification of the surface groups of the polymer, wherein said selective binding conditions include: the presence of a competition agent in solution, which competition agent has ionic groups having a lesser binding avidity for the abnormal form of the protein than does the polyionic material; a salt concentration not exceeding 250 mM and a pH of from 5 to 10.

2. A process as claimed in claim 1, wherein the binding agent is protease resistant.

3. A process as claimed in claim 1, wherein a protease is present during said binding or wherein said protein is exposed to the action of a protease after being bound.

4. A process as claimed in claim 1, wherein the binding agent is a polyanionic material having a multiplicity of anionic groups or a polycationic material having a multiplicity of cationic groups.

5. A process as claimed in claim 4, wherein said polyionic material has a multiplicity of anionic groups which are sulphate, carboxyl or phosphate groups or a multiplicity of cationic groups which are amino groups, imine groups or quaternary ammonium groups.

6. A process as claimed in claim 5, wherein the said polyionic material is a polyanionic polyglycoside.

7. A process as claimed in claim 6, wherein the polyanionic polyglycoside is a polysulphonated polyglycoside.

8. A process as claimed in claim 7, wherein the polyanionic polyglycoside is a polyanionic pentosan derivative or dextran derivative.

9. A process as claimed in claim 8, wherein the polysulphonated polyglycoside is pentosan polysulphate (PPS) or dextran sulphate.

10. A process as claimed in claim 4, wherein said polyionic material: is hexadimethrine bromide, PAMAM dendrimer, poly L-lysine, pDADMAC or polyethyleneimine.

11. A process as claimed in claim 1, wherein the competition agent has a lesser density of ionic groups than the polyionic material.

12. A process as claimed in claim 11, wherein the competition agent is anionic.

13. A process as claimed in claim 12, wherein the competition agent is an anionic detergent.

14. A process as claimed in claim 12, wherein the competition agent is an amino acid amide of a fatty acid.

15. A process as claimed in claim 14, wherein the competition agent is n-lauroylsarcosine.

16. A process as claimed in claim 1, wherein the pH is from 8 to 9.

17. A process as claimed in claim 1, wherein the pH is from 8.2 to 8.6.

18. A process as claimed in claim 1, wherein a detergent is present which promotes binding of the binding agent to the abnormal form of the protein.

19. A process as claimed in claim 1, wherein said binding agent after binding to said aggregated abnormal form of the protein is captured with an immobilised capture agent.

20. A process as claimed in claim 19, wherein said capture agent is a lectin or an antibody reactive with said binding agent.

21. A process as claimed in claim 19, wherein the said binding agent is provided with a selectively bindable tag moiety and said capture agent binds to said tag moiety.

22. A process as claimed in claim 21, wherein said bindable tag moiety is biotin, fluorescein, dinitrophenol, digoxygenin, a nucleic acid or nucleic acid analogue sequence or (His)6.

23. A process as claimed in claim 1, wherein the binding agent is immobilised to a solid medium prior to exposure to said abnormal form of the protein.

24. A process as claimed in claim 23, wherein the medium is a substrate having said binding agent coated thereon.

25. A process as claimed in claim 23, wherein the binding agent is provided with a selectively bindable tag moiety and is immobilised to said solid medium via said tag moiety.

26. A process as claimed in claim 25, wherein said bindable tag moiety is biotin, fluorescein, dinitrophenol, digoxygenin, a nucleic acid or nucleic acid analogue sequence or (His)6.

27. A process as claimed in claim 1, wherein said binding agent is a solid which provides a surface having said binding avidity.

28. A process as claimed in claim 1, which process further comprises detecting the selectively bound abnormal aggregating form of the protein present in the material.

29. A process as claimed in claim 1, wherein the pH is from 5.6 to 9.

30. A process as claimed in claim 1, wherein the pH is from 7 to 9.

* * * * *